April 18, 1944. V. G. McGUIGAN Plant Pat. 624
PEACH TREE
Filed June 26. 1943
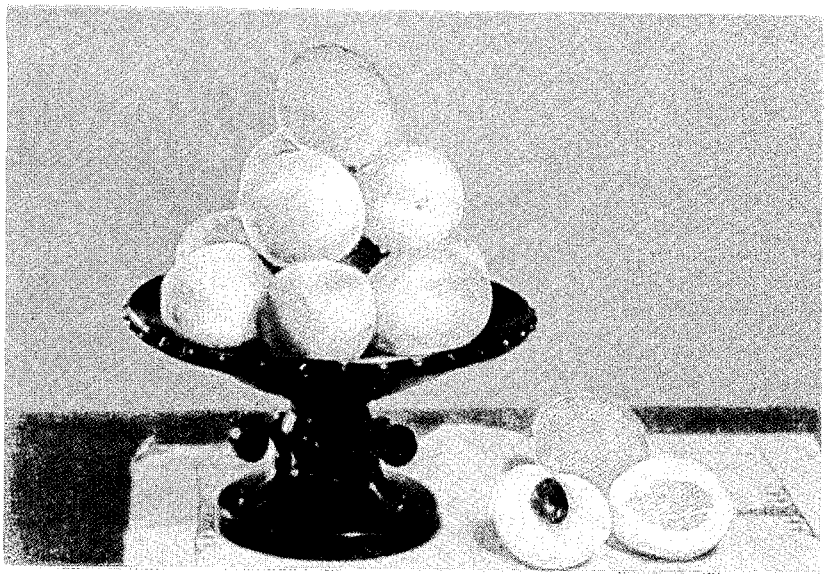
Inventor
V. G. McGuigan
By Robert Robb
Attorneys Patented Apr. 18, 1944

Plant Pat. 624

UNITED STATES PATENT OFFICE

624

PEACH TREE

Virgil Gladstone McGuigan, Cedar Springs, Ontario, Canada, assignor to E. D. Smith & Sons, Limited, Winona, Ontario, Canada Application June 26, 1943, Serial No. 492,455

1 Claim. (Cl. 47—62)

The present discovery relates to a new and distinct variety of peach tree, found by me growing upon a tree of the variety known as "Hills Chilli."

This peach, so far as the plant is concerned, resembles the "Belle of Georgia" in leaf and color, is hardy, vigorous of growth, bearing regularly and heavily, and is very resistant to disease and insects, as determined by observation in comparison with other varieties grown under comparable conditions in the same orchard.

The fruit of this new variety resembles the well known Elberta in size and shape, having a skin also somewhat characteristic of that of the Elberta variety; its coloring when firm is yellow, with red cheeks and red sifting throughout the skin; posseses a flavor and texture finer than Elberta; is dry-free stone; ships well, and is a good dessert fruit and a good canner, having especially unusual qualities as a commercial canner.

This new fruit ripens after "South Haven" and the three "V's" and before "Elberta," and further does not drop like "Elberta," but hangs on the tree until thoroughly ripe.

The accompanying drawing illustrates a group of specimens of this new variety, arranged to disclose the various features of the fruit as nearly as possible for the purposes of this disclosure.

By asexual reproduction the characteristics of the new variety have been found to be established.

The following is a detail description of this new variety, color designations being in accord with ordinary dictionary terminology; except where otherwise indicated:

Dates first and last picking: September 1st–September 10th.

Propagation: Holds its distinguishing characteristics through succeeding propagations by cuttings, grafting and budding.

Tree: Large; vigorous; spreading; open; vase formed; hardy; very productive; regular bearer.

*Trunk.*—Stocky; smooth.

*Branches.*—Stocky; medium smooth. *Color*—O–Y Hair Brown is nearest, Ridgway's Color Standard, Plate XLVI 17''''.

*Lenticels.*—Few; medium size.

*Leaves.*—Length—six inches; width—one and one-half inches; medium size; lanceolate; acutely pointed; thick; medium Green; smooth. *Margin*—glandular; crenate. *Petiole*—long; thick. *Glands*—four; opposite; large; reniform; Green; mostly on petiole. *Stipules*—not persistent.

*Flower Buds.*—Hardy; medium size; medium long; pointed; appressed; pubescent.

*Flowers.*—Dates first and full bloom—with medium peaches April 30th. Medium early; medium large; Pink. Self fertile.

Fruit: Maturity when described—eating ripe September 1st to 10th.

*Size.*—Uniform. Diameter, axial—2½ inches up; transverse in suture plane—2¾ inches; at right angles to suture plane—2¼ inches.

*Form.*—Uniform; oblong; narrowly compressed toward suture. *Suture*—distinct; extends from base but continues to apex over entire circumference; has slight depression beyond pistil point. *Ventral surface*—rounded slightly throughout both sides. *Lips*—equal. *Cavity*—abrupt; elongated in suture plane with suture showing on both sides. Depth—⅜ inch. Breadth—½ inch. Markings—none. *Base*—oblique. *Apex*—short; pistil point slightly apical.

*Stem.*—Length, $\frac{5}{16}$ inch; medium stout; glabrous. Adherence to stone—dry-free.

*Skin.*—Thin; medium tender; free. *Tendency to crack*—none in wet or dry season. *Color*—bright Yellow, sifted Red. *Down*—comparable to Elberta in this respect.

Flesh:

*Color.*—Yellow, mottled with Red next to stone. *Surface of pit cavity*—Red and dry, free.

*Amygdalin.*—Moderate. *Juice*—moderate; rich.

*Texture.*—Firm; fine; meaty.

*Fibres.*—Few; fine.

*Ripens.*—Even.

*Flavor.*—Mild.

*Aroma.*—Pronounced.

*Eating quality.*—Best.

Stone: Dry-free. *Fibres*—short. *Free*—on sides toward base; parts from flesh smoothly.

*Size.*—Medium. Length—1½ inches. Breadth—1 inch. Thickness—½ inch.

*Form.*—Elliptical.

*Base.*—Oblique. *Hilum*—narrow. *Apex*—Rounded.

*Sides.*—Unequal; flattened on left side. *Surface*—regularly furrowed toward apex throughout; ridged near base toward apex throughout.

*Ridges.*—Jagged.

*Pits.*—Elongated. *Ventral edge*—thick throughout. *Dorsal edge*—narrow with narrow groove. *Ridges on either side*—interrupted.

*Color of stone.*—Reddish Brown.

*Tendency to split.*—Very slight in wet or dry season.

Use: Market; dessert; canning; good shipper, dessert, and splendid canner.

Keeping quality: Good.

Resistance: To insects—very good. To diseases—very good. Resistant insofar as this is evidenced by absence of any disease throughout development and establishment of this variety.

Shipping quality: Good.

I claim:

A new and distinct variety of peach tree, characterized as to novelty by its hardiness, vigorous growth, resistance to disease and insects, and regular heavy bearing habits; skin of attractive color and comparable to "Elberta" with regard to pubescence; fine flavor and texture of the meat; dry-free stone; excellent shipping, eating and canning qualities; and persistence of the fruit to hang on tree until thoroughly ripe, all substantially as shown and described herein.

VIRGIL GLADSTONE McGUIGAN.